(12) United States Patent
Mulrooney

(10) Patent No.: US 12,419,568 B2
(45) Date of Patent: Sep. 23, 2025

(54) DEVICES FOR AND METHODS OF DIAGNOSIS AND/OR MONITORING DYSPHAGIA

(71) Applicant: Phagenesis Limited, Manchester (GB)

(72) Inventor: Conor Mulrooney, Manchester (GB)

(73) Assignee: Phagenesis Limited, Manchester (GB)

( * ) Notice: Subject to any disclaimer, the term of this patent is extended or adjusted under 35 U.S.C. 154(b) by 1037 days.

(21) Appl. No.: 16/922,229

(22) Filed: Jul. 7, 2020

(65) Prior Publication Data
US 2020/0330025 A1    Oct. 22, 2020

Related U.S. Application Data

(63) Continuation of application No. 15/750,686, filed as application No. PCT/GB2016/052389 on Aug. 4, 2016, now Pat. No. 10,743,810.

(30) Foreign Application Priority Data

Aug. 7, 2015 (GB) ..................................... 1513989
Dec. 7, 2015 (GB) ..................................... 1521538

(51) Int. Cl.
*A61B 5/00* (2006.01)
*A61J 15/00* (2006.01)
*A61N 1/05* (2006.01)
*A61N 1/36* (2006.01)

(52) U.S. Cl.
CPC .......... *A61B 5/4205* (2013.01); *A61B 5/6852* (2013.01); *A61J 15/0003* (2013.01); *A61J 15/0084* (2015.05); *A61N 1/0517* (2013.01); *A61N 1/36014* (2013.01); *A61N 1/36034* (2017.08)

(58) Field of Classification Search
None
See application file for complete search history.

(56) References Cited

U.S. PATENT DOCUMENTS

| 803,464 A | 10/1905 | Beck |
| 1,032,436 A | 7/1912 | Smith |
| 2,627,096 A | 2/1953 | Alessi |
| 2,779,985 A | 2/1957 | Turner et al. |
| 3,179,995 A | 4/1965 | Hawk |
| 3,630,195 A | 12/1971 | Santomieri |
| 3,839,841 A | 10/1974 | Amplatz |
| 3,894,706 A | 7/1975 | Mizusawa |

(Continued)

FOREIGN PATENT DOCUMENTS

| CA | 2594296 A1 | 3/2006 |
| CN | 203389196 U | 1/2014 |

(Continued)

OTHER PUBLICATIONS

Fraser, Chris et al., Driving Plasticity in Human Adult Motor Cortex is Associated with Improved Motor Function After Brian Injury, Neuron, vol. 34, 831-840, May 30, 2002.

(Continued)

*Primary Examiner* — Aurelie H Tu
(74) *Attorney, Agent, or Firm* — Fortem IP LLP

(57) ABSTRACT

The use of a device to measure patient sensory response through the application of an incrementally increased electrical current to the oropharynx.

4 Claims, 3 Drawing Sheets

(56) References Cited

U.S. PATENT DOCUMENTS

| | | |
|---|---|---|
| 3,951,136 A | 4/1976 | Wall |
| 4,025,015 A | 5/1977 | Kolic |
| 4,295,618 A | 10/1981 | Morota et al. |
| 4,381,011 A | 4/1983 | Somers |
| 4,453,545 A | 6/1984 | Inoue |
| 4,531,937 A | 7/1985 | Yates |
| 4,691,883 A | 9/1987 | Kurihara |
| 4,707,906 A | 11/1987 | Posey |
| 4,776,349 A | 10/1988 | Nashef et al. |
| 4,840,337 A | 6/1989 | Zaugg |
| 4,960,412 A | 10/1990 | Fink |
| 5,109,870 A | 5/1992 | Silny et al. |
| 5,125,904 A | 6/1992 | Lee |
| 5,147,315 A | 9/1992 | Weber |
| 5,179,952 A | 1/1993 | Buinevicius et al. |
| 5,201,903 A | 4/1993 | Corbett et al. |
| 5,372,131 A | 12/1994 | Heinen |
| 5,382,239 A | 1/1995 | Orr et al. |
| 5,389,074 A | 2/1995 | Parker et al. |
| 5,457,852 A | 10/1995 | Liu |
| 5,551,953 A | 9/1996 | Lattin et al. |
| 5,588,424 A | 12/1996 | Insler et al. |
| 5,755,225 A | 5/1998 | Hutson |
| 5,759,490 A | 6/1998 | Malchesky |
| 5,762,638 A | 6/1998 | Shikani et al. |
| 5,800,402 A | 9/1998 | Bierman |
| 5,836,895 A | 11/1998 | Ramsey |
| 5,957,968 A | 9/1999 | Belden et al. |
| 6,006,138 A | 12/1999 | Don |
| 6,148,222 A | 11/2000 | Ramsey |
| 6,259,938 B1 | 7/2001 | Zarychta et al. |
| 6,266,548 B1 | 7/2001 | Lamade et al. |
| 6,366,813 B1 | 4/2002 | DiLorenzo |
| 6,464,697 B1 | 10/2002 | Edwards et al. |
| 6,484,053 B2 | 11/2002 | Leelamanit et al. |
| 6,532,388 B1 | 3/2003 | Rakow et al. |
| 6,611,699 B2 | 8/2003 | Krueger |
| 6,613,025 B1 | 9/2003 | Palasis |
| 6,658,294 B1 | 12/2003 | Zadeh et al. |
| 6,804,866 B2 | 10/2004 | Lemke et al. |
| 6,856,822 B2 | 2/2005 | Larsson |
| 7,324,851 B1 | 1/2008 | DiLorenzo |
| 7,598,839 B1 | 10/2009 | Wedley |
| 7,871,430 B2 | 1/2011 | Pavcnik et al. |
| 7,918,828 B2 | 4/2011 | Lundgaard et al. |
| 8,048,062 B2 | 11/2011 | Adams et al. |
| 8,092,433 B2 | 1/2012 | Hamdy |
| 8,876,798 B2 | 11/2014 | Clark et al. |
| 8,968,331 B1 | 3/2015 | Sochor |
| 9,895,486 B1 | 2/2018 | Carey-Hench |
| 9,982,742 B2 | 5/2018 | Loewe et al. |
| 10,028,885 B2 | 7/2018 | Martin et al. |
| 10,285,341 B2 | 5/2019 | McCaslin et al. |
| 10,743,810 B2 | 8/2020 | Mulrooney |
| 10,888,690 B2 | 1/2021 | Mulrooney |
| 11,617,881 B2 | 4/2023 | Mulrooney et al. |
| 11,980,753 B2 | 5/2024 | Mulrooney et al. |
| 11,992,681 B2 | 5/2024 | Mulrooney |
| 2001/0039413 A1 | 11/2001 | Bowe |
| 2001/0054425 A1 | 12/2001 | Bertram |
| 2002/0032468 A1 | 3/2002 | Hill et al. |
| 2002/0065544 A1 | 5/2002 | Smits |
| 2002/0165537 A1 | 11/2002 | Kelley et al. |
| 2002/0177765 A1 | 11/2002 | Bowe et al. |
| 2003/0036794 A1 | 2/2003 | Ragheb et al. |
| 2004/0034396 A1 | 2/2004 | Asmar et al. |
| 2004/0073110 A1* | 4/2004 | Stewart .............. A61B 18/1492 600/437 |
| 2004/0162584 A1 | 8/2004 | Hill et al. |
| 2004/0220645 A1 | 11/2004 | Kretschmer et al. |
| 2004/0230162 A1 | 11/2004 | Tan |
| 2005/0098688 A1 | 5/2005 | Miarka et al. |
| 2005/0137459 A1 | 6/2005 | Chin et al. |
| 2005/0146676 A1 | 7/2005 | Silvestro |
| 2005/0192559 A1 | 9/2005 | Michels et al. |
| 2005/0229933 A1 | 10/2005 | McGrail et al. |
| 2006/0085049 A1 | 4/2006 | Cory et al. |
| 2007/0074728 A1 | 4/2007 | Rea |
| 2007/0089898 A1 | 4/2007 | Potter |
| 2007/0156041 A1 | 7/2007 | Rea |
| 2008/0009810 A1 | 1/2008 | Hamdy |
| 2008/0147013 A1 | 6/2008 | Breton et al. |
| 2008/0249507 A1 | 10/2008 | Hadani |
| 2008/0255441 A1 | 10/2008 | Hadani |
| 2008/0300530 A1 | 12/2008 | Massengale |
| 2009/0062772 A1 | 3/2009 | Wakeford et al. |
| 2009/0223698 A1 | 9/2009 | Gilliland et al. |
| 2009/0275825 A1 | 11/2009 | Thomas |
| 2009/0276025 A1 | 11/2009 | Burnes et al. |
| 2010/0115739 A1 | 5/2010 | Mathur |
| 2010/0170066 A1 | 7/2010 | Honeycutt |
| 2010/0174170 A1 | 7/2010 | Razavi |
| 2010/0206453 A1 | 8/2010 | Leeflang et al. |
| 2010/0218975 A1 | 9/2010 | Mehan |
| 2010/0317956 A1 | 12/2010 | Kartush |
| 2011/0137374 A1 | 6/2011 | Kieval et al. |
| 2011/0210215 A1 | 9/2011 | Nitsche et al. |
| 2011/0251519 A1 | 10/2011 | Romoscanu |
| 2012/0065469 A1 | 3/2012 | Allyn et al. |
| 2012/0203058 A1 | 8/2012 | Kanapkey et al. |
| 2012/0259208 A1 | 10/2012 | Bloom et al. |
| 2012/0260921 A1 | 10/2012 | Sangwan |
| 2013/0006323 A1 | 1/2013 | Tal et al. |
| 2013/0197321 A1 | 8/2013 | Wilson |
| 2013/0282078 A1 | 10/2013 | Wacnik |
| 2014/0000622 A1 | 1/2014 | Azagury et al. |
| 2014/0012235 A1 | 1/2014 | Pinchuk et al. |
| 2014/0128936 A1 | 5/2014 | Laufer et al. |
| 2014/0276663 A1 | 9/2014 | Pinchuk et al. |
| 2014/0288382 A1 | 9/2014 | Lemmens et al. |
| 2014/0288384 A1 | 9/2014 | Mulrooney |
| 2014/0303617 A1 | 10/2014 | Shimada |
| 2014/0378941 A1 | 12/2014 | Su |
| 2015/0224280 A1 | 8/2015 | Pinchuk et al. |
| 2017/0050014 A1 | 2/2017 | Rizik |
| 2017/0224986 A1 | 8/2017 | Imran et al. |
| 2017/0312497 A1 | 11/2017 | Mulrooney et al. |
| 2018/0214672 A1 | 8/2018 | Mulrooney |
| 2018/0235533 A1 | 8/2018 | Mulrooney |
| 2019/0038894 A1 | 2/2019 | Bassi et al. |
| 2019/0134380 A1 | 5/2019 | Mulrooney |
| 2019/0134389 A1 | 5/2019 | Mulrooney |
| 2020/0061369 A1 | 2/2020 | Mulrooney et al. |
| 2020/0061370 A1 | 2/2020 | Mulrooney et al. |
| 2020/0179045 A1 | 6/2020 | Levin et al. |
| 2020/0306528 A1 | 10/2020 | Linden et al. |
| 2021/0077784 A1 | 3/2021 | Mulrooney |
| 2021/0077808 A1 | 3/2021 | Mulrooney et al. |
| 2022/0160537 A1 | 5/2022 | Mulrooney |
| 2022/0161029 A1 | 5/2022 | Mulrooney |
| 2022/0161030 A1 | 5/2022 | Mulrooney |
| 2022/0313981 A1 | 10/2022 | Mulrooney |
| 2023/0181023 A1 | 6/2023 | Mulrooney |
| 2023/0302244 A1 | 9/2023 | Mulrooney |
| 2023/0405324 A1 | 12/2023 | Mulrooney |
| 2024/0009451 A1 | 1/2024 | Mulrooney |
| 2024/0299746 A1 | 9/2024 | Mulrooney |

FOREIGN PATENT DOCUMENTS

| | | |
|---|---|---|
| CN | 203954394 U | 11/2014 |
| CN | 204319485 U | 5/2015 |
| EP | 0510857 A1 | 10/1992 |
| EP | 0571514 A1 | 12/1993 |
| EP | 1179307 A2 | 2/2002 |
| EP | 2253350 A1 | 11/2010 |
| EP | 2693968 A1 | 2/2014 |
| EP | 3331597 A1 | 6/2018 |
| GB | 2169206 A | 7/1986 |
| GB | 2254253 A | 10/1992 |
| GB | 2294642 A | 5/1996 |
| GB | 2313316 A | 11/1997 |
| GB | 2532044 A | 5/2016 |
| GB | 2541039 A | 2/2017 |

(56) References Cited

FOREIGN PATENT DOCUMENTS

| | | |
|---|---|---|
| JP | S63200771 A | 8/1988 |
| JP | H05115563 A | 5/1993 |
| JP | H07500523 A | 1/1995 |
| JP | H08505291 A | 6/1996 |
| JP | H10118190 A | 5/1998 |
| JP | 2005312969 A | 11/2005 |
| JP | 2012512722 A | 6/2012 |
| JP | 2014068716 A | 4/2014 |
| WO | 9400050 A1 | 1/1994 |
| WO | 9405361 A1 | 3/1994 |
| WO | 9526777 A1 | 10/1995 |
| WO | 9715349 A1 | 5/1997 |
| WO | 9719667 A1 | 6/1997 |
| WO | 03026741 A1 | 4/2003 |
| WO | 2005051472 A2 | 6/2005 |
| WO | 2006024825 A1 | 3/2006 |
| WO | 2007129002 A1 | 11/2007 |
| WO | 2009154718 A1 | 12/2009 |
| WO | 2010023579 A1 | 3/2010 |
| WO | 2010071812 A1 | 6/2010 |
| WO | 2010091440 A2 | 8/2010 |
| WO | 2012131303 A1 | 10/2012 |
| WO | 2013109835 A1 | 7/2013 |
| WO | 2014152808 A1 | 9/2014 |
| WO | 2015027094 A1 | 2/2015 |
| WO | 2017089752 A1 | 6/2017 |
| WO | 2022106843 A1 | 5/2022 |
| WO | 2022106844 A1 | 5/2022 |

OTHER PUBLICATIONS

Bath et al., Pharyngeal electrical stimulation for neurogenic dysphagia following stroke, traumatic brain injury or other causes: Main results from the PHADER cohort study, EClinical Medicine 28 (2020) 100608, 9 pages.

Bath et al., Pharyngeal Electrical Stimulation for Treatment of Dysphagia in Subacute Stroke a Randomized Controlled Trial, Stroke, Jun. 2016, vol. 47, Issue 6, pp. 1562-1570.

Dziewas et al., Design and implemental of Pharyngeal electrical Stimulation for early de-cannulation in TRACheotomized (PHAST-TRAC) stroke patients with neurogenic dysphagia, International Journal of Stroke, 12(4), 2017, pp. 430-437.

Dziewas et al., PHAryngeal electrical STimulation for early decannulation in TRACheotomised patients with neurogenic dysphagia after stroke (PHAST-TRAC): a prospective, single-blinded, randomised trial, Lancet Neurology, vol. 17, Issue 10, 2018, 29 pages.

Essa et al., The BDNF polymorphism VAL66Met may be predictive of swallowing improvement post pharyngeal electrical stimulation in dysphagic stroke patients, Neurogastroenterol Motil, 2017; 27, 7 pages.

Fraser et al., Differential changes in human pharyngoesophageal motor excitability induced by swallowing, pharyngeal stimulation, and anesthesia, Am J Physiol Gastrointest Liver Physiol, 285: G-137-G144, 2003.

Hamdy et al., The cortical topography of human swallowing musculature in health and disease, Nature Medicine, vol. 2, No. 11, Nov. 1996, pp. 1217-1224.

Hamdy, et al., Long-term reorganization of human motor cortex driven by short-term sensory stimulation, Nature Neuroscience, vol. 1, No. 1, May 1998, pp. 64-68.

Jayasekeran et al., Adjunctive Functional Pharyngeal Electrical Stimulation Reverses Swallowing Disability After Brain Lesions, Gastroenterology, 2010; vol. 138, No. 5, pp. 1737-1746.

Koestenberger, et al., A Pilot Study of Pharyngeal Electrical Stimulation of Orally Intubated ICU Patients with Dysphagia, Neurocrit Care (2020) 32: 532-538.

Magara et al., Tu1254 Does Combining Pharyngeal Electrical Stimulation With Simultaneous Swallowing of Carbonated Liquids Enhance the Cortical Swallowing Motor System?, Gastroenterology, Apr. 2016 [Abstract only].

Magara, et al., Exploring the effects of synchronous pharyngeal electrical stimulation with swallowing carbonated water on cortical excitability in the human pharyngeal motor system, Neurogastroenterol Motil (2016), 11 pages.

Restivo et al., Pharyngeal electrical stimulation device for the treatment of neurogenic dysphagia: technology update, Medical Devices: Evidence and Research, 2018: 11, pp. 21-26.

Restivo et al., Pharyngeal Electrical Stimulation for Dysphagia Associated with Multiple Sclerosis: A Pilot Study, Brain Stimulation 6, 2013, pp. 418-423.

Sasegbon et al., Advances in the Use of Neuromodulation for Neurogenic Dysphagia: . . . , American Journal of Speech-Language Pathology, Jul. 2020, vol. 29, pp. 1044-1064.

Scutt, et al., Pharyngeal Electrical Stimulation for Treatment of Poststroke Dysphagia: Individual Patient Data Meta-Analysis of Randomised Controlled Trials, Stroke Research and Treatment, 2015, 8 pages.

Suntrup et al., Electrical pharyngeal stimulation for dysphagia treatment in tracheotomized stroke patients: a randomized controlled trial, Intensive Care Med (2015) 41: 1629-1637.

Suntrup-Krueger et al., Electrical pharyngeal stimulation increases substance P level in saliva, Neurogastroenterol Motil (2016) 28, pp. 855-860.

Vasant et al., Pharyngeal Electrical Stimulation in Dysphagia Poststroke: A Prospective, Randomized Single-Blinded Interventional Study, Neurorehabilitation and Neural Repair, 2016, vol. 30(9), pp. 866-875.

Gow, David , et al., "Characterising the Central Mechanisms of Sensory Modulation in Human Swallowing Motor Cortex", Clinical Neurophysiology, Elsevier Science, IE, vol. 115, No. 10, Jun. 26, 2004, pp. 2382-2390.

Hamdy, S. , et al., "Modulation of human swallowing behaviour by thermal and chemical stimulation in health and after brain injury", Neurogastroenterol Motil, vol. 15, No. 1, Feb. 2003, pp. 69-77.

Hamdy, Shaheen , et al., "Recovery of Swallowing After Dysphagic Stroke Relates to Functional Reorganization in the Intact Motor Cortex", Gastroenterology, vol. 115, No. 5, Nov. 1998, pp. 1104-1112.

Jasper, Herbert H., "The Ten Twenty Electrode System of the International Federation", Clinical Neurophysiol, vol. 10, pp. 370-375.

Kajii, Yuka , et al., "Sour taste stimulation facilitates reflex swallowing from the pharynx and larynx in the rat", Physiology & Behavior, vol. 77, No. 2-3, 2002, pp. 321-325.

Takeuchi, Hiro-Aki , et al., "Electrophysiological and Behavioral Studies of Taste Discrimination in the Axolotl (*Ambystoma mexicanum*)", Physiology & Behavior, vol. 56, No. 1, Jul. 1994, pp. 121-127.

Tutuian, R. , et al., "Effects of position on oesophageal function: studies using combined manometry and multichannel intraluminal impedance", Neurogastroenterol Motil., vol. 15, No. 1, Feb. 2003, pp. 63-67.

Wassermann, Eric M., "Risk and safety of repetitive transcranial magnetic stimulation: report and suggested guidelines from the International Workshop on the Safety of Repetitive Transcranial Magnetic Stimulation, Jun. 5-7, 1996", Electroencephalography and clinical Neurophysiology, vol. 108,, 1998, pp. 1-16.

Great Britain Search Report for GB Application No. 1521538.7, Dated Mar. 29, 2016, 4 pages.

PCT Search Report and Written Opinion of PCT Application No. PCT/GB2016/052389, Dated Nov. 2, 2016, 17 pages.

International Search Report for Appl No. GB1513792.0 dated Jan. 4, 2016, 4 pages.

International Search Report for Appl No. GB1521538.7 dated Mar. 29, 2016, 5 pages.

International Search Report for Appl No. GB1513797.9 dated Jan. 19, 2016, 3 pages.

Wilmskoetter, Janina , et al., "Cortical and Subcortical Control of Swallowing—Can We Use Information From Lesion Locations to Improve Diagnosis and Treatment for Patients With Stroke?", American journal of speech-language pathology vol. 29,2S (2020): 1030-1043. (Year: 2020).

(56) References Cited

OTHER PUBLICATIONS

Takeishi, et al., "Effects of Pharyngeal Electrical Stimulation on Swallowing Performance", PLOS One 13(1): e0190608. https://doi.org/10.1371/journal.pone.0190608 (Year: 2018),.

* cited by examiner

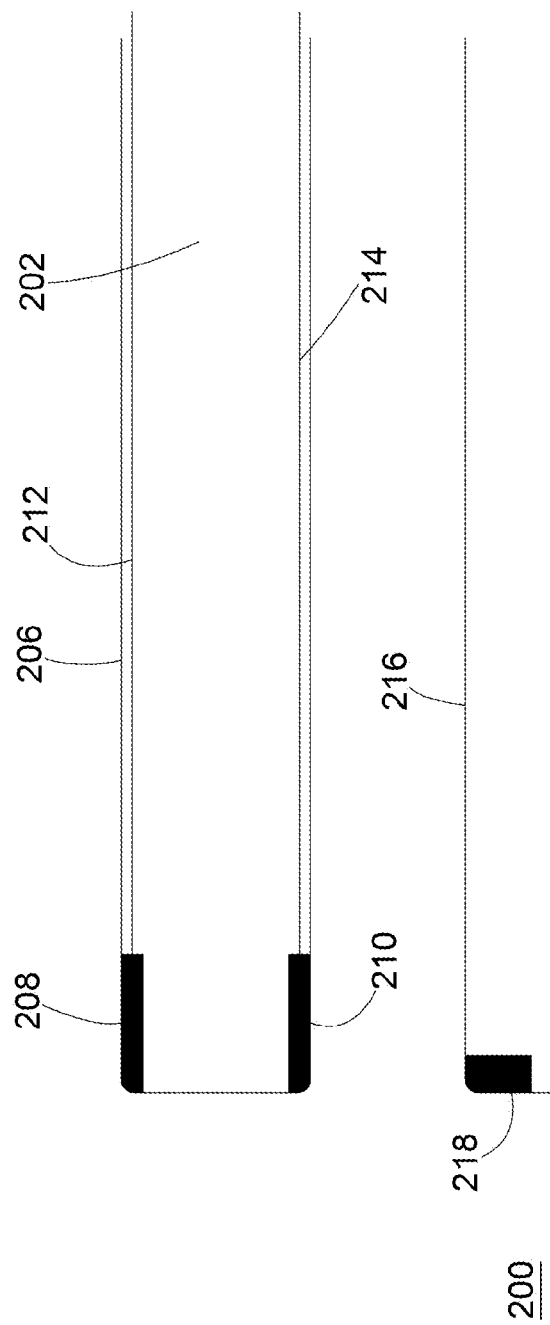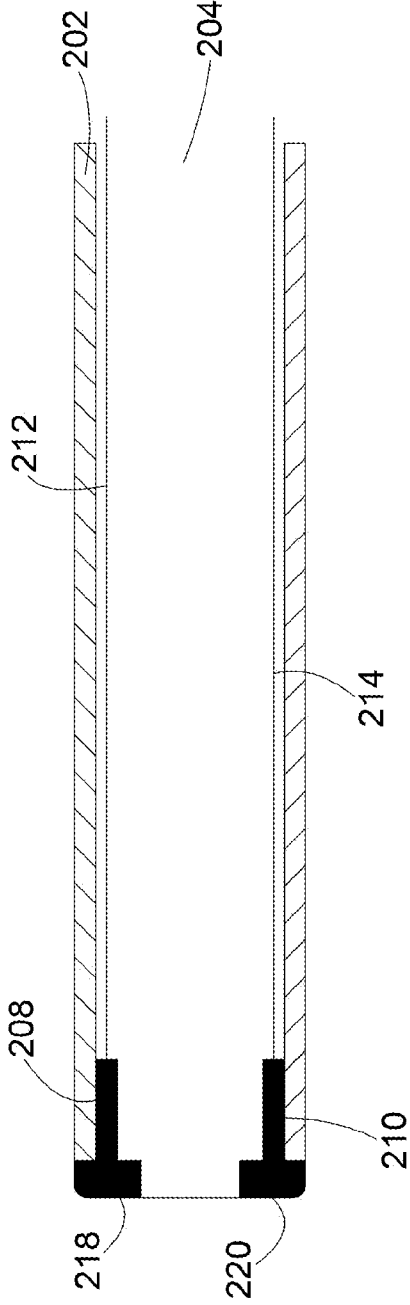

DEVICES FOR AND METHODS OF DIAGNOSIS AND/OR MONITORING DYSPHAGIA

RELATED APPLICATIONS

This application is a continuation of national phase application Ser. No. 15/570,686 filed on Feb. 6, 2018 under 35 USC § 371 of PCT Application No. PCT/GB2016/052389 with an International filing date of Aug. 4, 2016, which claims priority of GB Patent Applications GB 1513989.2, filed Aug. 7, 2015, and GB 1521538.7, filed Dec. 7, 2015. Each of these applications is herein incorporated by reference in its entirety for all purposes.

FIELD OF THE INVENTION

The present invention relates to devices for and methods of diagnosis and/or monitoring dysphagia.

BACKGROUND OF THE INVENTION

Dysphagia is a medical term given to an inability to swallow or an inability to swallow in a safely controlled way. It has been reported that 7%-10% of all adults older than 50 years of age present with clinically significant dysphagia. Of those over the age of 60, this increases to 14% of the entire adult population. In total 10 million Americans are evaluated each year in clinics and hospitals for swallowing difficulties. It has also been reported that >51% of institutionalised elderly patients present with oropharyngeal dysphagia.

Collectively these figures reflect the fact that neurogenic dysphagia (dysphagia arising from neurological damage) can develop due to a very wide range of underlying conditions such as traumatic brain injury, cerebral palsy, head and neck cancer and neurodegenerative diseases like MS, Parkinson's and Alzheimer's. It is however stroke that is probably the most recognized single cause of dysphagia—greater than 50% of patients who have a stroke will present with dysphagia.

Complications that have been associated with dysphagia post-stroke include pneumonia, malnutrition, dehydration, poorer long-term outcome, increased length of hospital stay, increased rehabilitation time and the need for long-term care assistance, increased mortality, and increased health care costs. These complications impact the physical and social well being of patients, quality of life of both patients and caregivers, and the utilization of health care resources.

Dysphagia can be difficult to diagnose and to monitor. Symptoms may improve or worsen over even short periods of time. Gold standard diagnostic methods for swallowing assessment involve the use of instrumental exams that visualise the movement of materials from the oral spaces to the oesophagus. Examples of such methods include videofluoroscopy (VFS) and Fibroscopic Endoscopic Evaluation of Swallowing (FEES). These allow quantification of the time involved in the movement of a bolus of material through the oral spaces, the amount of swallowed material that pools in the pharynx and the amount of material that enters into the airways. They can also capture the response of the patient to material entering into the airways as a determinant of level of awareness the patient has to this risk associated event and their ability to respond to it. These methods can be difficult or traumatic for the patient and require substantial expertise and training.

Other diagnostic methods include bedside assessments such as the Toronto Bedside Swallow Test (TORBST). These are observational methods that test the ability of the subject to swallow a variety of different materials. These methods are more qualitative in nature and are designed to screen for the presence or absence of a normal swallow. Whilst they have the advantage of being easy to carry out they lack the diagnostic sensitivity of instrumental methods and in particular are poor at identifying so called silent aspirators whose sensory processes are so compromised they do not react to even substantial amounts of material entering the airways.

The pharyngeal phase of swallowing is initiated voluntarily. This first requires input and oversight from the parts of the brain involved in motor planning. These higher centres receive information about the nature of the material, size of the bolus etc., and modulate the involuntary sequences that will follow. The duration and intensity of muscle contraction can be modified to accommodate a larger bolus for example. Only when the food or liquid bolus is voluntarily pushed through the faucial pillars (the structures to the left and right of the uvula), or in older individuals, when the food is in contact with the base of the tongue, is the reflexive involuntary component of the pharyngeal swallow triggered. This is where the central pattern generator within the medulla (brain stem), modulated by the higher centres comes into play. The reflexive sequence that follows has two key functions: i) controlled passage of food or secretions from the pharynx to the oesophagus; and ii) airway protection.

A common manifestation in neurogenic dysphagia is that whilst the pattern generating processes that control the sequence of activities in swallowing (located in the brain stem) may be intact, the triggers to begin or modulate the swallowing processes are absent or compromised. This can reflect the fact that the sensory input provided by the bolus of material at the back of the throat or base of the tongue is no longer sufficient to be detected and to trigger the reflexive swallowing process. In effect the sensory threshold for that individual has been raised. Whilst the consequences of this increase in sensory threshold may be seen with existing diagnostic methods, the increase and absolute level of the threshold is not measured by these methods.

Pharyngeal Electrical Stimulation (PES) is a method for treating neurogenic dysphagia. It involves the application of electrical stimulation to the pharyngeal mucosa and this results in an increase in activity in the motor cortex and other areas of the brain. These changes facilitate a functional reorganisation of the centres in the brain responsible for controlling and coordinating swallow function.

SUMMARY OF THE INVENTION

As used herein, the term patient sensory response data shall be interpreted as meaning the patient's sensory threshold, i.e. the weakest electrical current that a patient can detect.

As used herein, the term control sensory response data shall be interpreted as meaning either: i) a sensory response range as would be expected from a healthy individual who is not suffering from dysphagia, ii) a sensory response range as would be expected from an individual suffering from dysphagia or ii) at least one previous patient sensory response data entry obtained from a specific patient and in the case of multiple data entries obtained from a patient over time, said data entries are plotted on a curve to indicate the extent and speed of recovery from dysphagia by comparing the slope of the curve with other control sensory response data obtained from other patients who exhibited recovery from dysphagia.

An aspect of the present invention provides a device for diagnosing dysphagia, the device comprising: a catheter for oral or nasal insertion into a patient, the catheter comprising an elongate body having at least one electrode mounted on or about the elongate body, said at least one electrode configured to receive a variable electrical current for applying electrical stimulation to the patient's oropharynx, and a control unit comprising an electrical current generator, a non-volatile memory for storing patient sensory response data and control sensory response data, means for recording the patient's sensory response to the applied electrical stimulation and a processor for comparing the patient's sensory response to a control sensory response and determining whether the patient is suffering from dysphagia and/or monitoring the patient's recovery from dysphagia.

Another aspect of the present invention provides a device for diagnosing and/or treating dysphagia, the device comprising: a control unit, and a catheter for oral or nasal insertion into a patient, and wherein the catheter comprises a nasal gastrointestinal feeding tube and a sleeve selectively movable relative to the feeding tube, the sleeve having at least one electrode mounted thereon, said at least one electrode configured to receive a variable electrical current for applying electrical stimulation to the patient's oropharynx, and a control unit comprising an electrical current generator, a non-volatile memory for storing patient sensory response data and control sensory response data, means for recording the patient's sensory response to the applied electrical stimulation and a processor for comparing the patient's sensory response to a control sensory response and determining whether the patient is suffering from dysphagia and/or monitoring the patient's recovery from dysphagia.

Another aspect of the present invention provides a method of diagnosing dysphagia, the method comprising: i) applying an electrical current of between 1 mA and 50 mA to a patient's oropharynx; ii) increasing the current incrementally; iii) obtaining patient sensory feedback after each incremental increase in current; iv) comparing the patient's sensory response with a control sensory response; and v) determining whether the patient is suffering from dysphagia and/or monitoring the patient's recovery from dysphagia.

Devices and methods of the present invention enable a medical professional to make a diagnosis of dysphagia and/or monitor a patient's recovery from dysphagia. Over time, patient's suffering from dysphagia may show signs of clinical improvement whether as a result of treatment, such as pharyngeal electrical stimulation, or through spontaneous recovery. The applicant has observed that an improvement in swallowing ability, i.e. an improvement in the patient's clinical condition, broadly corresponds to a reduction in the patient's sensory response, i.e. the patient's sensory threshold is lower. During treatment a patient would be expected to exhibit a reducing sensory threshold and this trend would be indicative of a corresponding improvement in swallowing function. The same trend would be observable in patient's who have not received treatment but whose clinical condition has spontaneously improved.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIGS. 3a, 3b and 3c show a third embodiment of a device according to the present invention.

DETAILED DESCRIPTION

Figure 1:
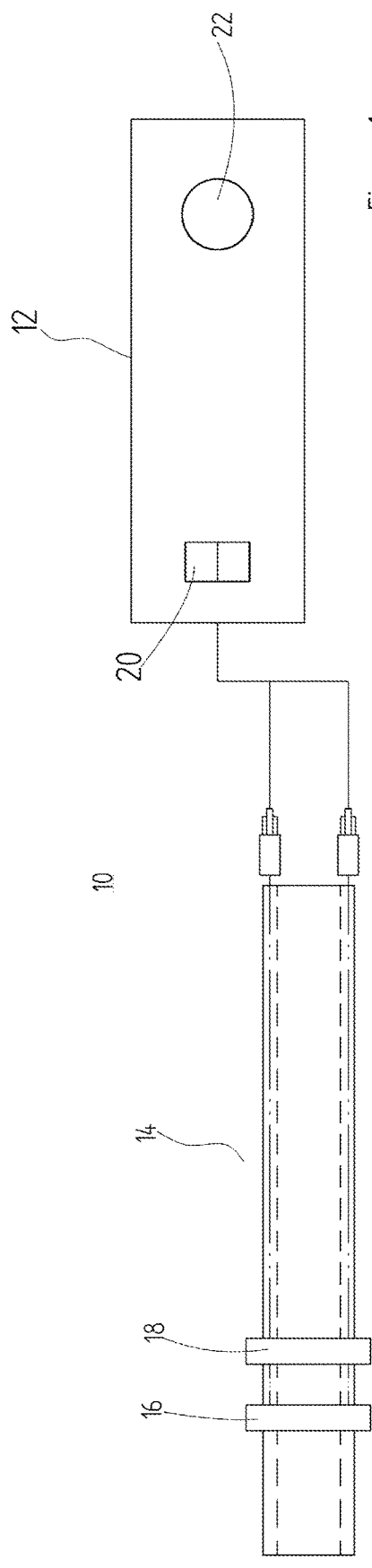
FIG. 1 shows a first embodiment of a device according to the present invention.

FIG. 1 shows a device (10) for diagnosing dysphagia. The device (10) comprises a control unit (12) and a catheter (14). The control unit (12) comprises a variable electric current generating means for delivering electrical current to the catheter (14). The control unit (12) further comprises a non-volatile memory for storing patient sensory response data and/or control sensory response data and a processing means for comparing and/or processing patient sensory response data against said control sensory response data to make a diagnostic determination of whether a patient is suffering from dysphagia and/or monitoring the patient's recovery from dysphagia.

The catheter (14) has a at least one electrode (16,18) mounted thereon. The at least one electrode (16,18) is electrically connected to the variable electric current generating means of the control unit (12). The catheter (14) may be single use or re-usable.

In embodiments of the invention described with reference to FIG. 1, the device (10) may be configured to provide Pharyngeal Electrical Stimulation (PES) and to provide a recommendation for further treatment based on patient sensory response.

Figure 2:
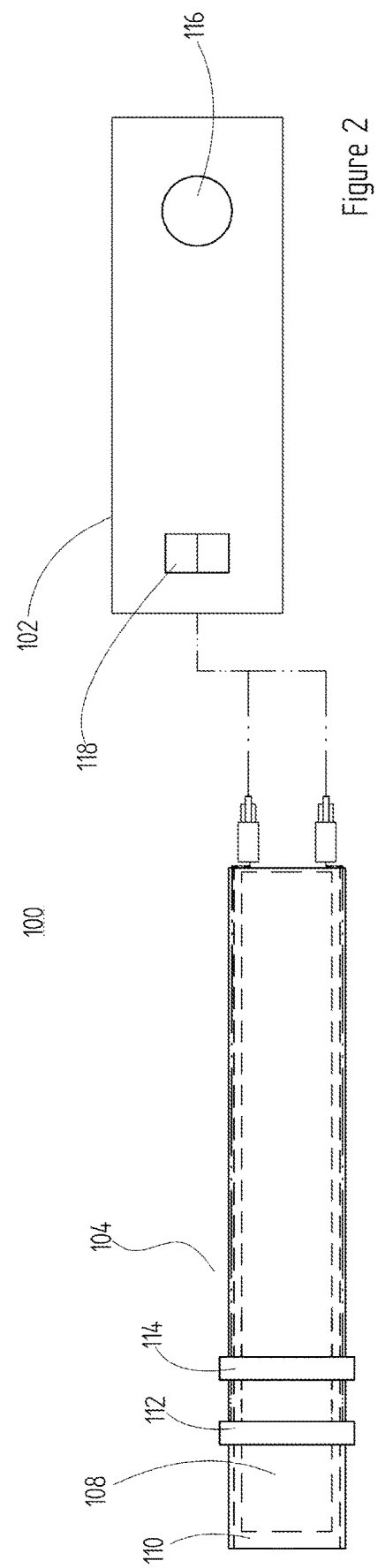
FIG. 2 shows a second embodiment of a device according to the present invention.

FIG. 2 shows a device (100) for diagnosing dysphagia and for providing nutrition. The device (100) comprises a control unit (102) and a catheter (104). The control unit (102) comprises a variable electric current generating means for delivering electrical current to the catheter (104). The control unit (102) further comprises a non-volatile memory for storing patient sensory response data and/or control sensory response data and a processing means for comparing and/or processing patient sensory response data against control sensory response data to make a diagnostic determination of whether a patient is suffering from dysphagia and/or to monitor the patient's recovery from dysphagia.

The catheter (104) comprises a NG feeding tube (108) and a sleeve (110) selectively movable relative to the NG feeding tube (108). The sleeve (110) carries at least one electrode (112,114) and wiring connecting the at least one electrode (112,114) to the control unit (102).

Each of the devices (10, 100) of FIGS. 1 and 2 are either provided with a rechargeable battery (not shown) or are electrically connectable to a power source, or both. Each device (10, 100) is also provided with a power selector (20, 118) to turn the device (10, 100) on/off and a control means (22, 116) to select the level of current to be delivered to the at least one electrode (18, 112). In some embodiments a graphical display is provided to visually identify to a medical professional that a patient is suffering from dysphagia and/or to indicate a change in the patient's clinical condition.

In other embodiments a speaker is provided to audibly identify to a medical professional that a patient is suffering from dysphagia and/or to indicate a change in the patient's clinical condition. In other embodiments the device (10, 100) is equipped with wireless communications technology to transmit information relating to diagnosis and treatment to a server, network or independent device such as smartphone, tablet or laptop. The wireless communications technology could be WIFI, Bluetooth or GSM, for example, but is not limited thereto.

Each device (10, 100) has a diagnostic mode for diagnosing whether a patient is suffering from dysphagia and/or for monitoring a change in the patient's clinical condition. The control unit (12, 102) collects patient sensory response data and stores said data against a specific patient record in the non-volatile memory of the device (10, 100). The control unit (12, 102) can therefore compare instantaneous patient sensory response data against control sensory response data to monitor a patient's response to PES over time to determine whether or not further PES is required.

The device (10, 100) is turned on by activation of the power selector (20, 116). The control means (22, 116) is used to select the current level and is typically set to a current level that is not detectable by a patient, i.e. 1 mA. The catheter is inserted orally or nasally into the patient and the at least one electrode (16,18,112,114) is aligned with the patient's oropharynx.

The control means (22, 116) is used to activate the at least one electrode (14, 112) and impart the 1 mA electrical current into the patient's tissue. The control means (22, 116) is then used to increase the electrical current in 1 mA increments up to a maximum of 50 mA. After each increment the patient will be requested to confirm whether they can sense the electric current or not. If the patient cannot sense the electric current it will be increased by a further 1 mA. If the patient can sense the electric current the current level will be recorded as patient sensory response data.

When using the device (10, 100), the patient sensory data will be saved in the non-volatile memory against that individual patient's record. In certain embodiments the non-volatile memory is integral to the device (10, 100) and data contained therein is uploaded to a remote server either wirelessly or by plugging the device (10, 100) into a separate device connected to a server. Such a device (10, 100) can also store patient data uploaded thereto from a server or other device. Such data can be used by the device (10, 100) to compare patient sensory response data against control sensory response data. Such comparison is used by the device (10, 100) to diagnose dysphagia by comparing patient sensory response data to control sensory response data. The device (10,100) can be used to monitor unassisted recovery from dysphagia and recovery as a result of PES.

FIG. 3 shows a device (200) for applying electrical stimulation to a patient's oropharynx. The device (200) comprises a re-usable probe (202), as detailed in FIG. 3a, and a disposable sleeve (204), as detailed in FIG. 3b. The re-usable probe (202) comprises a tubular body (206), which may be rigid, semi-rigid or flexible, and a pair of terminally located electrodes (208,210). Conducting wires (212,214) are connected between each electrode (208,210) and an electrical current generator (not shown).

The disposable sleeve (204) comprises a hollow tubular body (216) closed at one end. The closed end of the tubular body includes one or more areas (218,220) that are capable of conducting an electric current from the electrodes (208, 210) through the sheath in the direction of the longitudinal axis of the device (200).

In use, as shown in FIG. 3c, the probe (202) is inserted into the sleeve (204) so that the pair of electrodes (208,210) are aligned and substantially in contact with the one or more conductive areas (218,220) of the sleeve (204).

Studies

Studies were conducted in two patient groups; a treatment arm and a control arm. Each patient in the treatment arm received a stimulation level that is specifically tailored to their treatment needs. This level is determined through first establishing their sensory threshold and thereafter their tolerance level (the highest level of applied stimulation the patient can tolerate for the treatment period). A suitable stimulation level is then derived from these two parameters.

A randomised controlled trial of PES in the control arm consisting of 30 subjects with dysphagia and a tracheotomy was performed to assess whether treatment resulted in sufficient restoration of safe swallowing to allow the tracheotomy cannula to be removed. As part of this study the threshold and tolerance levels of subjects in both the treatment and control arms were recorded.

Figure 4:
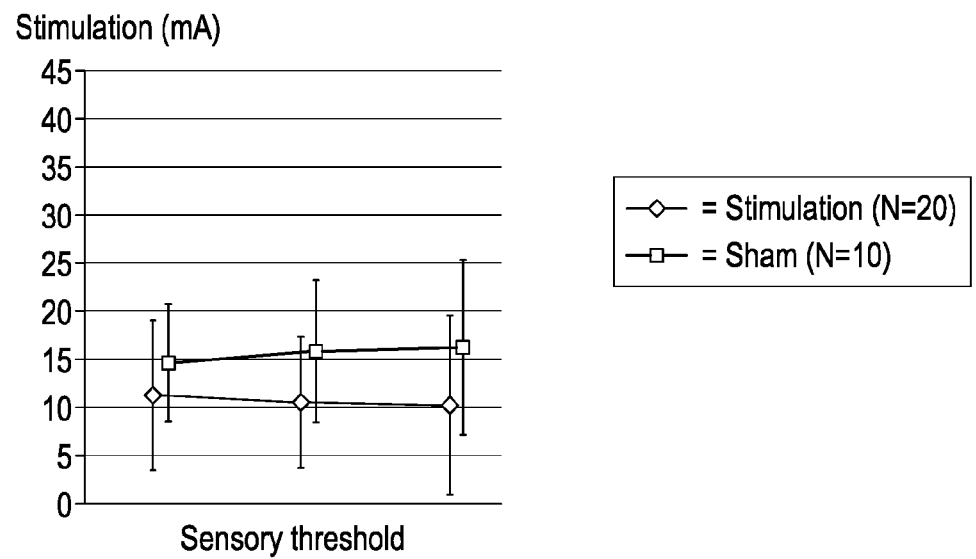
FIG. 4 shows sensory threshold levels in treated and untreated subjects over three consecutive days whereby the treated group also improved their swallow function.

FIG. 4 shows the initial and subsequent mean threshold levels for the treatment (Stimulation) arm and the control (Sham) arms. It can be seen that whilst the initial sensory threshold levels were similar, over the course of treatment the sensory threshold levels in the group receiving stimulation decreased whilst those not receiving stimulation actually increased.

This data suggests that decreasing sensory threshold levels are linked to swallowing recovery and that the trend in sensory level over time may also be indicative of the extent to which the subject is responding to treatment.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A device for determining whether a patient is suffering from dysphagia, the device comprising:
    a catheter comprising:
        a probe comprising an elongate body having at least one electrode mounted thereon,
        a sleeve comprising a hollow elongate body formed from a non-conductive material and configured to receive the probe, and at least one conductive area which, in use, is aligned with the at least one electrode to enable an electrical current from the at least one electrode to pass through the at least one conductive area, and
        wherein the catheter is configured to be positioned within the patient's oropharynx such that delivery of the electrical current to the at least one electrode and the at least one conductive area applies electrical stimulation to oropharyngeal tissue proximate the at least one conductive area of the sleeve; and
    a control unit comprising:
        an electrical current generator configured to be electrically coupled to the at least one electrode to deliver the electrical current to the at least one electrode and the at least one conductive area,
        a non-volatile memory for storing patient sensory response data and control sensory response data, wherein the patient sensory response data comprises a weakest electrical current that the patient can detect when the catheter is positioned within the patient's oropharynx and applying the electrical stimulation to the oropharyngeal tissue, and a processor for comparing the patient's sensory response data to the control sensory response data stored in the non-volatile memory and, based on the comparison, determining whether the patient is suffering from dysphagia.

2. The catheter according to claim 1, wherein the at least one electrode is terminally located on the probe.

3. The catheter according to claim 2, wherein the at least one conductive area of the sleeve directs the electrical current from the at least one electrode in a direction of a longitudinal axis of the catheter.

4. The catheter according to claim 1, wherein the probe is reusable and the sleeve is disposable.

\* \* \* \* \*